(12) United States Patent
Foo et al.

(10) Patent No.: US 8,855,742 B2
(45) Date of Patent: Oct. 7, 2014

(54) METHODS AND SYSTEMS FOR TRACKING AN INTERVENTIONAL DEVICE

(75) Inventors: Thomas Kwok-Fah Foo, Clifton Park, NY (US); Robert David Darrow, Scotia, NY (US); Florian Wiesinger, Freising (DE)

(73) Assignee: General Electric Company, Niskayuna, NY (US)

( * ) Notice: Subject to any disclaimer, the term of this patent is extended or adjusted under 35 U.S.C. 154(b) by 66 days.

(21) Appl. No.: 13/563,724

(22) Filed: Jul. 31, 2012

(65) Prior Publication Data

US 2014/0039299 A1     Feb. 6, 2014

(51) Int. Cl.
*A61B 5/055*     (2006.01)
(52) U.S. Cl.
USPC ........................................................ 600/417
(58) Field of Classification Search
USPC ........................................................ 600/417
See application file for complete search history.

(56) References Cited

U.S. PATENT DOCUMENTS

| | | | |
|---|---|---|---|
| 5,715,822 A | 2/1998 | Watkins et al. | |
| 6,845,261 B2 * | 1/2005 | Pettersson et al. | 600/413 |
| 7,912,531 B1 | 3/2011 | Chiu et al. | |
| 2007/0007957 A1 | 1/2007 | Tamaroff et al. | |
| 2007/0156042 A1 | 7/2007 | Unal | |
| 2007/0167726 A1 * | 7/2007 | Unal et al. | 600/410 |
| 2007/0249934 A1 | 10/2007 | Aksit et al. | |
| 2008/0097189 A1 | 4/2008 | Dumoulin et al. | |
| 2008/0114235 A1 | 5/2008 | Unal et al. | |
| 2010/0312096 A1 | 12/2010 | Guttman et al. | |

FOREIGN PATENT DOCUMENTS

WO     2007078409 A1     7/2007

OTHER PUBLICATIONS

Dewan, M. et al., "Deformable Motion Tracking of Cardiac Structures (DEMOTRACS) for Improved MR Imaging", Computer Vision and Pattern Recognition, 2007. CVPR '07. IEEE Conference, Issue Date: Jun. 17-22, 2007, on pp. 1-8.

* cited by examiner

*Primary Examiner* — Long V. Le
*Assistant Examiner* — Kevin Pontius
(74) *Attorney, Agent, or Firm* — Seema S. Katragadda

(57) ABSTRACT

Embodiments of a method, a tracking system, an MRI system, and a non-transitory computer readable medium that stores instructions for simultaneous imaging and tracking are presented. A designated signal and one or more characteristics corresponding to a plurality of imaging gradient waveforms are received. Further, a tracking pulse sequence is synchronized with an imaging pulse sequence at a determined point based on the designated signal. The tracking pulse sequence is then applied simultaneously with the imaging pulse sequence for acquiring corresponding response signals from an interventional device that includes at least one tracking coil and a tracking source configured to generate response signals at a tracking resonant frequency different from an imaging resonant frequency. A location of the tracking coil within or outside body of a subject is determined based on the response signals received from the tracking source and the characteristics corresponding to the imaging gradient waveforms.

32 Claims, 6 Drawing Sheets

METHODS AND SYSTEMS FOR TRACKING AN INTERVENTIONAL DEVICE

BACKGROUND

Embodiments of the present disclosure relate generally to magnetic resonance (MR) imaging, and more particularly to systems and methods for tracking an interventional device using MR imaging.

Medical interventional procedures are widely used for managing a plurality of life-threatening medical conditions. Particularly, minimally invasive interventional procedures are being exceedingly employed as cost-effective alternatives to invasive surgery. During an interventional procedure, an interventional device such as an endovascular catheter or needle may be inserted into a vascular structure that provides access to a region of interest (ROI), such as a cardiac region of a patient. The insertion as well as navigation of the interventional device within different branches of a vascular system, however, is a challenging procedure.

Accordingly, certain interventional techniques employ imaging modalities such as computed tomography (CT) and MR imaging (MRI) for generating high-fidelity images in near real-time to aid in guided interventions. Particularly, use of MRI during interventional procedures provides enhanced characterization of soft tissues, bone marrow, brain and spine without use of ionizing radiation typically used by CT systems. Additionally, MRI allows for accurate localization of the interventional device, which in turn, aids in accurate navigation of the interventional device within the vascular system without injuring surrounding tissues.

Conventionally, MRI systems employ passive and/or active techniques for tracking the interventional device within the patient's body. The passive techniques, for example, include use of paramagnetic markers and intravascular contrast agents for use in visualizing the interventional device. However, spatial and temporal resolutions achieved using the passive techniques are often acquisition dependent, and thus, may prove inadequate for distinguishing between the patient anatomy and the interventional device. Additionally, certain MRI systems employ active tracking techniques that typically provide higher signal-to-noise ratio and spatial and temporal resolutions than passive techniques. These active techniques, for example, include placing a radiofrequency (RF) receive coil on the interventional device and/or using a guide wire as a linear receive coil.

Generally, a small RF tracking coil is mounted on the interventional device such that the tracking coil is sensitive to protons in the immediate vicinity, for example, in surrounding blood or tissues. The MRI system, thus, tracks the position of the interventional device based on the position of the tracking coil. Specifically, the MRI system tracks the tracking coil by exciting spins of the protons and sequentially applying gradients in a plurality of orthogonal directions to localize the origin of the MR signals received from the tracking coil. To that end, the MRI system employs a separate tracking sequence with a fixed repetition period and at least three separate acquisitions to account for positional measurements along x, y and z directions.

Certain MRI systems implement the tracking sequence between successive image acquisitions. However, as typical image acquisition time extends over 1000 milliseconds, tracking of the interventional device may be delayed, thus making MR tracking unsuitable for real-time guidance of the interventional device. Certain other MRI systems interleave image acquisition with tracking to control latency. Interleaving of imaging and tracking acquisitions, however, interrupts imaging steady state. Accordingly, interleaving entails use of several dummy RF excitations to restore the imaging steady state for artifact-free imaging. The dummy RF excitations, however, add to the imaging time and tracking complexity.

Furthermore, conventional MRI systems typically employ a common Larmor or resonant frequency for imaging the surrounding tissue and tracking the interventional device, which may impede distinction between the interventional device and the surrounding tissue. Accordingly, a currently available approach is drawn to use of a single tracking coil adapted for use with both protons and other tracking nuclei. Merely using another tracking nuclei, however, may decrease MR coil quality factor leading to reduced coil sensitivity, which in turn, may hamper image quality.

BRIEF DESCRIPTION

In accordance with aspects of the present disclosure, a method for simultaneous imaging and tracking is presented. The method includes receiving a designated signal and one or more characteristics corresponding to a plurality of imaging gradient waveforms. Further, a tracking pulse sequence is synchronized with an imaging pulse sequence at a determined point in the imaging pulse sequence based on the designated signal. Moreover, the tracking pulse sequence is applied simultaneously with the imaging pulse sequence for acquiring corresponding response signals from an interventional device, where the interventional device comprises at least one tracking coil and a tracking source configured to generate the response signals at a tracking resonant frequency different from an imaging resonant frequency. A location of the tracking coil within or outside body of a subject is then determined based on the response signals received from the tracking source and the one or more characteristics corresponding to the imaging gradient waveforms.

In accordance with certain other aspects of the present disclosure, a tracking system is disclosed. The tracking system includes an interventional device configured to be inserted into body of a subject and at least one tracking coil operatively coupled to the interventional device. Further, the tracking system also includes a tracking source operatively coupled to one or more of the interventional device and the at least one tracking coil and configured to generate a magnetic resonance signal at a tracking resonant frequency different from an imaging resonant frequency. Additionally, the tracking system includes at least one processing subsystem. The processing subsystem may be configured to receive a designated signal and one or more characteristics corresponding to a plurality of imaging gradient waveforms. Further, the processing subsystem may be configured to synchronize a tracking pulse sequence with an imaging pulse sequence at a determined point in the imaging pulse sequence based on the designated signal. Additionally, the processing subsystem may be configured to apply the tracking pulse sequence simultaneously with the imaging pulse sequence for acquiring corresponding response signals from the tracking source at the tracking resonant frequency. The processing subsystem may also be configured to determine a location of the tracking coil within or outside the body of the subject based on the response signals received from the tracking source and the one or more characteristics corresponding to the imaging gradient waveforms.

In accordance with further aspects of the present disclosure, an MRI system is described. The MRI system includes a scanner comprising a plurality of coils configured to generate a magnetic field, one or more gradient fields and a plurality of radiofrequency signals within the magnetic field.

The MRI system also includes a processing subsystem configured to process magnetic resonance signals emitted from a target ROI of a subject positioned in the magnetic field in response to the plurality of radiofrequency signals and generate one or more corresponding images of the target ROI. Further, the MRI system also includes a tracking source operatively coupled to one or more of the interventional device and the at least one tracking coil and configured to generate a magnetic resonance signal at a tracking resonant frequency different from an imaging resonant frequency. Additionally, the MRI system includes at least one tracking controller. The tracking controller may be configured to receive a designated signal and one or more characteristics corresponding to a plurality of imaging gradient waveforms. Further, the tracking controller may be configured to synchronize a tracking pulse sequence with an imaging pulse sequence at a determined point in the imaging pulse sequence based on the designated signal. Additionally, the tracking controller may be configured to apply the tracking pulse sequence simultaneously with the imaging pulse sequence for acquiring corresponding response signals from the tracking source at the tracking resonant frequency. The tracking controller may also be configured to determine a location of the tracking coil within or outside the body of the subject based on the response signals received from the tracking source and the one or more characteristics corresponding to the imaging gradient waveforms. Moreover, the tracking controller may be configured to generate one or more images representative of the determined location of the tracking coil within the body of the subject for display. Further, the MRI system may also include a display device configured to display the one or more images of the target region of interest, the determined location of the tracking coil, or a combination thereof.

In accordance with certain aspects of the present disclosure, a non-transitory computer readable medium that stores instructions executable by one or more processors to perform a method for simultaneous imaging and tracking is presented.

A non-transitory computer readable medium that stores instructions executable by one or more processors to perform a method for simultaneous imaging and tracking. Based on the instructions, a designated signal and one or more characteristics corresponding to a plurality of imaging gradient waveforms is received. Further, a tracking pulse sequence is synchronized with an imaging pulse sequence at a determined point in the imaging pulse sequence based on the designated signal. Moreover, the tracking pulse sequence is applied simultaneously with the imaging pulse sequence for acquiring corresponding response signals from an interventional device, where the interventional device comprises at least one tracking coil and a tracking source configured to generate the response signals at a tracking resonant frequency different from an imaging resonant frequency. A location of the tracking coil within or outside body of a subject is then determined based on the response signals received from the tracking source and the one or more characteristics corresponding to the imaging gradient waveforms.

DRAWINGS

These and other features, and aspects of embodiments of the present disclosure will become better understood when the following detailed description is read with reference to the accompanying drawings in which like characters represent like parts throughout the drawings, wherein.

DETAILED DESCRIPTION

The following description presents exemplary systems and methods for simultaneous imaging and tracking during an interventional procedure. Particularly, embodiments illustrated hereinafter disclose an independent tracking system that may be readily coupled to an MRI system for simultaneously imaging a target ROI and tracking an interventional device. Additionally, the embodiments described herein also disclose a method for tracking an interventional device in real-time without disrupting an MR imaging sequence originally employed by the MRI system.

Although exemplary embodiments of the present systems and methods are described in the context of medical interventional procedures, it will be appreciated that use of the embodiments of the present system and method in various other imaging applications and systems is also contemplated. By way of example, some of these systems and applications may include non-destructive testing, fluid flow monitoring and/or other chemical and biological applications. An exemplary environment that is suitable for practising various implementations of the present system is discussed in the following sections with reference to FIG. 1.

Figure 1:
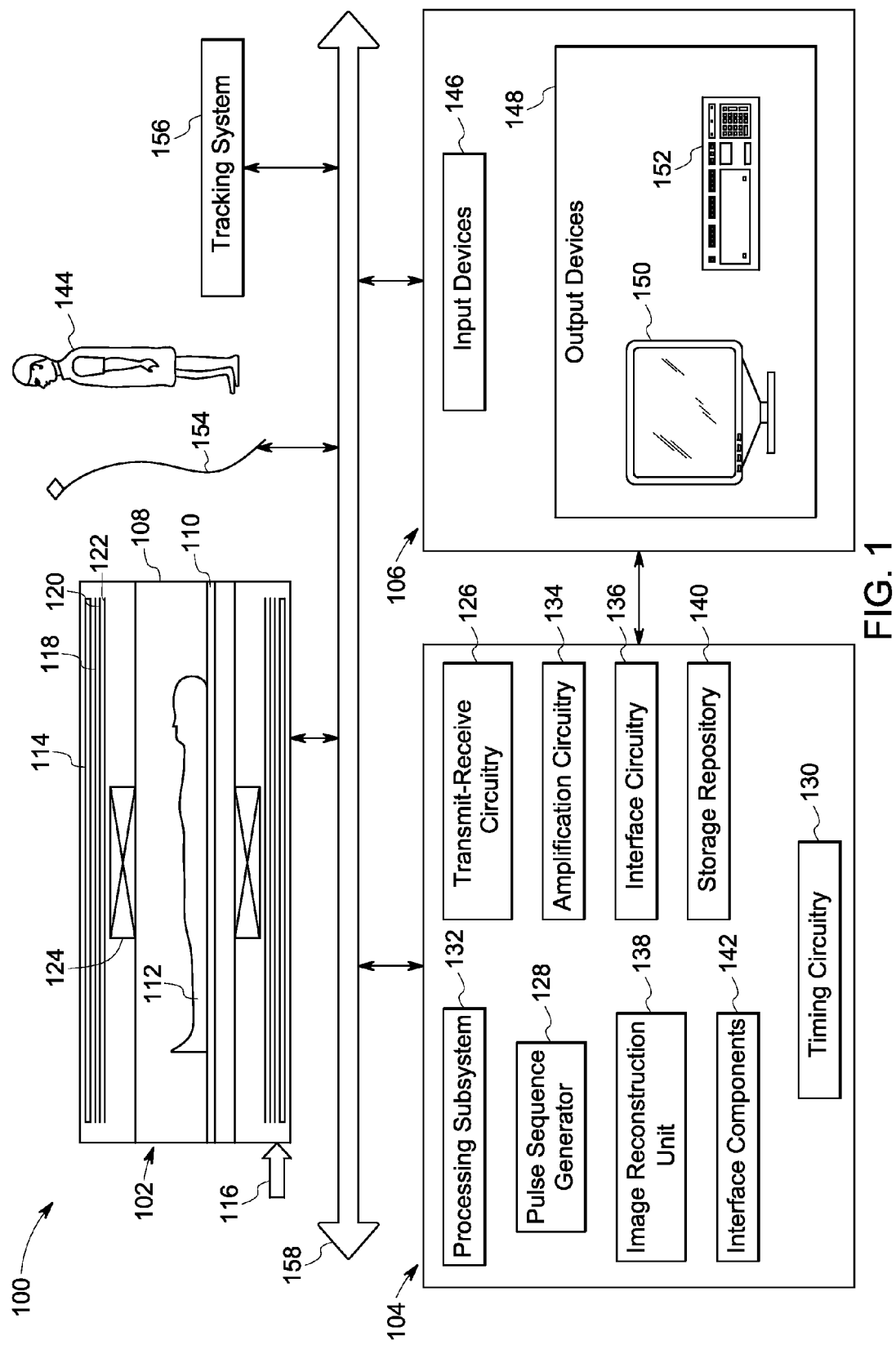
FIG. 1 is a schematic representation of an exemplary MRI system operatively coupled to an independent tracking system, in accordance with aspects of the present disclosure.

Specifically, FIG. 1 illustrates an MRI system 100 for use in interventional imaging. To that end, the MRI system 100 includes a scanner 102, a system controller 104 and an operator interface 106. Although the embodiment illustrated in FIG. 1 depicts a full body scanner 102, in certain embodiments, the MRI system 100 may include any suitable MRI scanner based on specific imaging and/or examination requirements. Further, a presently contemplated configuration of the MRI system 100 is drawn to a horizontal cylindrical bore imaging system employing a superconducting primary field magnet assembly. Certain other embodiments, however, may employ various other system configurations based on specific imaging mandates. The MRI system 100, for example, may include scanners employing vertical fields generated by superconducting magnets, permanent magnets, electromagnets, or combinations thereof.

Additionally, while FIG. 1 illustrates a closed MRI system 100, certain embodiments of the present disclosure may also be used in an open MRI system designed to allow access to a physician, such as during interventional imaging. It may also be noted that in certain embodiments, the MRI system 100 may include any suitable MRI scanner configuration in lieu of the full body scanner 102 illustrated in FIG. 1 based on specific imaging and/or examination requirements.

Further, in certain embodiments, the scanner 102 may include a patient bore 108 into which a table 110 may be positioned for disposing a patient 112 in a desired position for scanning. Moreover, the scanner 102 may also include a series of associated coils for imaging the patient 112. Particularly, in one embodiment, the scanner 102 includes a primary magnet coil 114, for example, energized via a power supply 116 for generating a primary magnetic field generally aligned with the patient bore 108. The scanner 102 may further include a series of gradient coils 118, 120 and 122 grouped in a coil assembly for generating accurately controlled magnetic fields, the strength of which vary over a designated field of view (FOV) of the scanner 102.

Particularly, the gradient coils 118, 120 and 122 may have different physical configurations adapted for different functions in the MRI system 100. For example, in one embodiment, the gradient coils 118, 120 and 122 are configured to produce magnetic field gradients used for spatially encoding acquired signals. In certain embodiments, the gradient coils 118, 120 and 122 may have mutually orthogonal axes, allowing a linear field gradient to be imposed in any desired direction using an appropriate combination of the three gradient coils 118, 120 and 122. The field gradient may then be employed for various functions such as slice selection, frequency encoding and/or phase encoding during MR imaging.

Further, the scanner 102 may include an RF coil 124 for generating RF pulses for exciting a gyromagnetic material of interest, typically bound in tissues (gyromagnetic tissue material) of the patient 112. In certain embodiments, the RF coil 124 may also serve as a receiving coil. Accordingly, the RF coil 124 may be operationally coupled to transmit-receive circuitry 126 in passive and active modes for receiving emissions from the gyromagnetic tissue material and for applying RF excitation pulses, respectively. Alternatively, the MRI system 100 may include various configurations of receiving coils different from the RF coil 124. Such receiving coils may include structures specifically adapted for target anatomies, such as head, knee and/or chest coil assemblies. Moreover, receiving coils may be provided in any suitable physical configuration, such as including phased array coils.

In certain embodiments, the system controller 104 controls operation of the associated MR coils for generating desired magnetic field and RF pulses. To that end, in one embodiment, the system controller 104 may include a pulse sequence generator 128, timing circuitry 130 and a processing subsystem 132 for generating and controlling imaging gradient waveforms and RF pulse sequences employed during patient examination. In one embodiment, the system controller 104 may also include amplification circuitry 134 and interface circuitry 136 for controlling and interfacing between the pulse sequence generator 128 and the coils of scanner 102. The amplification circuitry 134 may include one or more amplifiers that process the imaging gradient waveforms for supplying desired drive current to each of the gradient coils 118, 120 and 122 in response to control signals received from the processing subsystem 132. In certain embodiments, the amplification circuitry 134 may also amplify and couple the generated RF pulses to the RF coil 124 for transmission.

In one embodiment, the RF coil 124 receives response signals emitted by excited nuclei in the tissues of the patient 112. To that end, the RF coil 124 may be tuned to an imaging resonant frequency of the patient nuclei, for example, to about 63.5 MHz for hydrogen in a 1.5 Tesla magnetic field. In such embodiments, where the RF coil 124 serves both to emit the RF excitation pulses and to receive MR response signals, the interface circuitry 136 may also include a switching device (not shown in FIG. 1) for toggling the RF coil 124 between active/transmitting mode and passive/receiving mode. Additionally, the interface circuitry 136 may include additional amplification circuitry for driving the RF coil 124 and for amplifying the response signals for further processing. In certain embodiments, the amplified response signals may be transmitted to the processing subsystem 132 for determining information for use in image reconstruction.

To that end, the processing subsystem 132, for example, may include one or more application-specific processors, graphical processing units (GPUs), digital signal processors (DSPs), microcomputers, microcontrollers, Application Specific Integrated Circuits (ASICs) and/or Field Programmable Gate Arrays (FPGAs). In one embodiment, the processing subsystem 132 may be configured to use a specific imaging protocol for customizing scan sequences and generating data indicative of the timing, strength and shape of the RF and gradient pulses produced. Additionally, the processing subsystem 132 may ascertain the timing and length of a data acquisition window in the imaging pulse sequence using the timing circuitry 130. The processing subsystem 132 may then process the response signals emitted by excited patient nuclei in response to the RF pulses.

By way of example, in one embodiment, the processing subsystem 132 may be configured to demodulate, filter and/or digitize the response signals for determining the image reconstruction information. To that end, the processing subsystem 132 may be configured to apply analytical routines to the processed information for deriving features of interest, such as location of a stenosis and structural and/or functional parameters such as blood flow in the target ROI. The processing subsystem 132 may be configured to transmit this information to an image reconstruction unit 138 to allow reconstruction of desired images of the target ROI. Additionally, the processing subsystem 132 may be configured to receive and process patient data from a plurality of sensors (not shown in FIG. 1), such as ECG signals from electrodes attached to the patient 112 for display and/or storage.

Accordingly, in certain embodiments, the system controller 104 may further include a storage repository 140 for storing the acquired data, reconstructed images and/or information derived therefrom. The storage repository 140 may also store physical and logical axis configuration parameters, examination pulse sequence descriptions and/or programming routines for use during the scanning sequences implemented by the scanner 102. To that end, the storage repository 140 may include devices such as a hard disk drive, a floppy disk drive, a compact disk-read/write (CD-R/W) drive, a Digital Versatile Disc (DVD) drive, a flash drive and/or a solid-state storage device.

In one embodiment, the system controller 104 may include interface components 142 for exchanging the stored information such as scanning parameters and image data with the operator interface 106. Further, in certain embodiments, the operator interface 106 may allow an operator, such as an interventional practitioner 144 to specify commands and scanning parameters for use during the interventional procedure. To that end, the operator interface 106 may include one or more input devices 146 such as a keyboard and/or a panel that allows the interventional practitioner 144 to configure the system controller 104 to control imaging parameters such as table motion, patient and table orientation, and/or shape and timing of the RF pulse sequences.

Moreover, in certain embodiments, the operator interface 106 may also include output devices 148 such as a display 150 including one or more monitors and/or printers 152. The display 150, for example, may be integrated into wearable eyeglasses, or may be ceiling or cart mounted to allow the interventional practitioner 144 to observe the reconstructed images, data derived from the images and other relevant information such as scanning time throughout the procedure. In one embodiment, the display 150 includes an interactive user interface that may allow selection and display of scanning modes, FOV and prior exam data. The interactive user interface on the display 150 may also allow on-the-fly access to patient data such as respiration and heart rate, scanning parameters and selection of an ROI for subsequent imaging.

Particularly, during an interventional procedure, MR imaging allows determination of structural and/or functional information of the target ROI for diagnosis and/or treatment. Structural information such as location and size of a stenosis and functional information such as tissue perfusion parameters are very useful in ascertaining the pathological condition of the target ROI. The interventional practitioner 144 may rely on these functional parameters before the surgical procedure to plan for appropriate therapeutic measures to be applied during endovascular treatments such as cerebral vascular accidents and angioplasties. The interventional practitioner 144 may also use the functional parameters during the interventional procedure for evaluating effect of therapy in near real-time, and further for determining whether to stop or continue the procedure based on the evaluated effect.

Accordingly, the interventional practitioner 144 may employ the MRI system 100 to provide information and/or high-fidelity images for performing an interventional procedure on the patient 112. During the interventional procedure, the interventional practitioner 144 may insert a minimally invasive interventional device 154 into an access site such as a vascular structure that provides access to the target ROI of the patient 112. In one embodiment, the access site may be in close proximity to the target ROI. In an alternative embodiment, however, the access site may be at a distance from the target ROI such that there is little or no overlap between the imaging FOV of the scanner 102 and the area of access of the interventional practitioner 144.

In certain embodiments, the movement of the interventional device 154 from the access site to the target ROI may be independently tracked using an exemplary tracking system 156. Particularly, the tracking system 156 may allow for simultaneous imaging and tracking operations without interrupting and/or changing the imaging protocol used by the MRI system 100. To that end, the tracking system 156, the interventional device 154 and one or more components of the MRI system 100 may be operationally coupled to each other over a communications network 158 that includes a backplane bus or a wired and/or wireless network such as the Internet and a virtual private network. An exemplary embodiment of the interventional device 154 and the tracking system 156 suitable for practising various implementations of the present system will be discussed in greater detail with reference to FIGS. 2-3.

Figure 2:
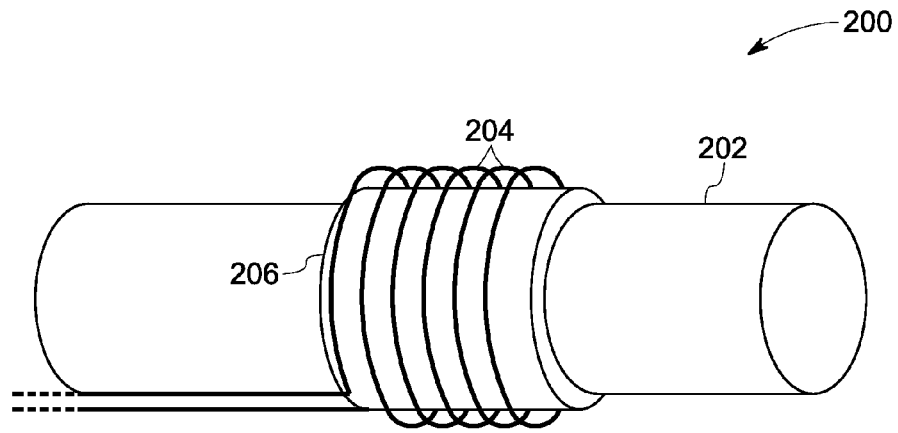
FIG. 2 is a diagrammatic representation of an exemplary embodiment of an interventional device for performing an MR-guided interventional procedure, in accordance with aspects of the present disclosure.

FIG. 2 illustrates an exemplary embodiment 200 of the interventional device 154 of FIG. 1 for performing an MR-guided interventional procedure at the target ROI of the patient 112 (see FIG. 1). In one embodiment, the interventional device 200 may be an external device positioned outside the body of the patient 112 and configured to be combined with a catheter, a needle, a laproscope, an endoscope, a stent, a shunt, a guide wire, a catheter sheath and/or a biopsy guidance device. Accordingly, in one example, the external interventional device 200 may include a biopsy needle holder positioned outside the body of the patient 112 and configured for correcting an angulation or trajectory of a biopsy needle. In another example, the external interventional device 200 may include a pointing device and/or an external surgical tool such as a laser, a cauterizer and/or a surface electrode.

However, in certain other embodiments, the interventional device 200 may be a device configured to be positioned inside the body of the patient 112. Accordingly, the interventional device 200, for example, may include a guide wire, a catheter, a catheter sheath, a needle, an endoscope, a laproscope, a stent, a shunt, an ablation device, or other similar devices suitable for use in a confined medical or surgical environment such as a body cavity, an orifice or a blood vessel.

Specifically, in the embodiment depicted in FIG. 2, the interventional device 200 includes a catheter 202, which may further include a catheter sheath and/or a guide wire (not shown). Additionally, in certain embodiments, the interventional device 200 may include at least one RF tracking coil 204. In one embodiment, the tracking coil 204, for example, may be a microcoil suitable for wrapping around and/or mounting at an operative end of the catheter 202. The relatively small size of the tracking coil 204 allows localization to a small region of sensitivity, thus, allowing the tracking coil 204 to receive MR signals from excited spins in the immediate vicinity to improve tracking of the tracking coil 204 in the patient's body. The location of the tracking coil 204, in turn, may be used to determine the location of a tip and/or orientation of the interventional device 200 within the patient's body.

Although the embodiment illustrated in FIG. 2 depicts only one tracking coil 204, in certain other embodiments, the interventional device 200 may include more than one tracking coil. Further, each of the tracking coils that are operationally coupled to the interventional device 200 allows for signal transmission and reception via separate transmission and reception channels in the tracking system 156 (See FIG. 1). Additionally, the transmission and reception channels used by the tracking coils may be different from the transmission and reception channels used by the MRI system 100 for imaging the target ROI.

Further, in certain embodiments, the tracking coil 204 may also serve as a transmitting coil for generating RF pulses for exciting the tissue or a material capable of generating the MR signal. Accordingly, in one embodiment, the tracking coil 204 may be operationally coupled to the transmit-receive circuitry 126 (see FIG. 1) in passive and/or active modes for receiving emissions from the interventional device 200 and for applying RF excitation pulses, respectively. However, as previously noted, the insertion and navigation of the interventional device 200 within the patient's body entails accuracy and swiftness for ensuring success of the interventional procedure. However, tracking the interventional device 200 using the same gyromagnetic material, for example protons present in tissues, used for image data acquisition may interfere with the imaging sequence and/or affect spin dynamics of imaging magnetization. This interference reduces the overall MRI signal, thus resulting in image artifacts that compromise image quality.

Accordingly, in one embodiment, the interventional device 200 may include a tracking source 206 such as a tracking sample that provides an MR signal at a resonant frequency different from the resonant frequency of spins of protons used for imaging. Generally, the tracking sample 206 may include a material having suitable nuclei with an odd number of nucleons and having a non-zero gyromagnetic ratio. Specifically, these materials may include nuclei such as Hydrogen ($^1$H), Helium-3 ($^3$He), Fluorine ($^{19}$F), Sodium ($^{23}$Na), Oxygen ($^{16}$O) and Xenon ($^{129}$Xe). In certain embodiments, the tracking sample 206 may have a higher gyromagnetic ratio and/or higher spin density than protons or any other material used for imaging such that signals received from the interventional device 200 and the target imaging ROI can be differentiated.

Furthermore, in one embodiment, the tracking sample 206 may be positioned in an encapsulated or embedded annular ring within the tracking coil 204 to avoid interference with the operation of the catheter 202. The interventional device 200, thus, provides the functionality of the catheter 202, guidewire and/or catheter sheath while allowing positional tracking by the one or more tracking coils 204 mounted along the length of the catheter 202.

However, unlike the RF coil 124 (see FIG. 1) tuned to the resonant frequency of hydrogen, in one embodiment, the tracking coil 204 may be tuned to receive MR signals processing at the resonant frequency (tracking resonant frequency) of the tracking sample 206. By way of example, when Fluorine is used as the tracking sample 206, the tracking coil 204 may be tuned to a frequency of about 60.08 MHz in a 1.5 Tesla magnetic field. Use of the tracking sample 206 having the tracking resonant frequency different from the imaging resonant frequency, thus, may allow for the tracking of the interventional device 200 to be independent of the image data acquisition by the MRI system 100. Additionally, when the imaging resonant frequency and the tracking resonant frequency are different, the RF pulses applied for tracking will have no effect on the spins in the target ROI. Moreover, incorporating the tracking sample 206 as a part of the interventional device 200 prevents corruption or diminishing of the tracking signals due to fast-flowing blood in the vasculature.

Conventionally, tracking data corresponding to the position of the interventional device 200 within the patient's body is ascertained using specialized RF tracking pulse sequences. These specialized tracking pulse sequences may include custom tracking gradient waveforms and data acquisition windows for tracking the interventional device. Particularly, in certain MRI systems, the specialized tracking pulse sequences are applied either after each imaging pulse sequence or interleaved between the imaging pulses to allow for simultaneous imaging and tracking. However, the interleaved imaging and tracking decreases the temporal resolution of the tracking acquisition as the tracking acquisition will be spread out over a greater temporal period.

As previously noted, use of such specialized tracking sequences in conventional MRI systems either renders MRI-aided tracking unsuitable for real-time interventional guidance or interrupts imaging steady state. Interruption of the imaging steady state may lead to image artifacts. These image artifacts may be minimized by extending the imaging sequence through additional scanning for restoring the imaging steady state. The extended imaging, however, increases the scan time and decreases the temporal resolution for both the imaging and tracking sequences. In contrast to such conventional MRI systems that entail disruption to the imaging steady state and/or changes to imaging configurations originally stored on the MRI systems, embodiments of the tracking system 156 disclosed herein allow for independent device tracking.

Figure 3:
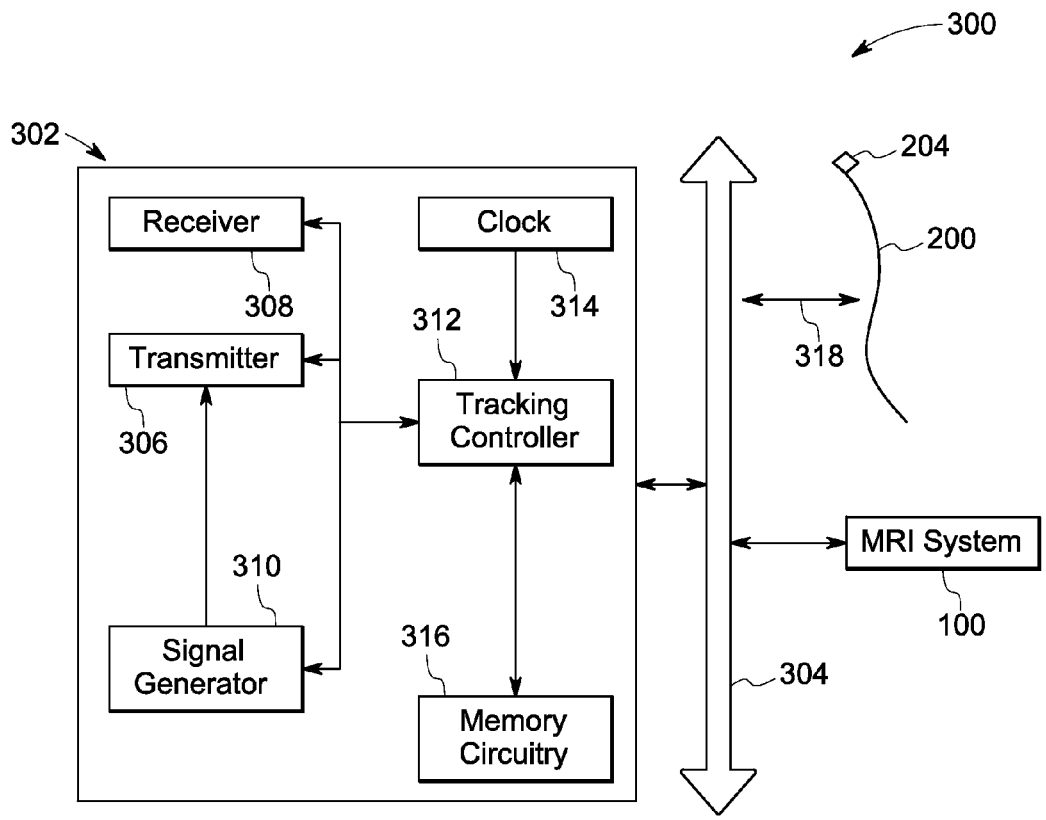
FIG. 3 is a schematic representation of exemplary components of the independent tracking system, such as the tracking system of FIG. 1, in accordance with aspects of the present disclosure.

FIG. 3 illustrates a schematic representation 300 of an exemplary embodiment of an independent tracking system 302, such as the tracking system 156 of FIG. 1. In one embodiment, the tracking system 302 may be communicatively coupled to the MRI system 100 (see FIG. 1), for example, as an add-on toolkit. As previously noted, in certain embodiments, the tracking system 302 may be communicatively coupled to the tracking coil 204 (see FIG. 2) and the MRI system 100 over a communication link 304. However, unlike conventional tracking systems that typically employ imaging circuitry of the MRI system 100 for device tracking, the tracking system 302 may be a self-contained unit that tracks movement of the interventional device 200 (see FIG. 2) within the patient's body without interrupting and/or changing the imaging protocol used by the MRI system 100.

To that end, in one embodiment, the tracking system 302 may include an RF transmitter 306, a receiver 308, a signal generator 310, a tracking controller 312, a clock 314 and memory circuitry 316 for independently imaging and tracking the interventional device 200. Although FIG. 3 illustrates only a few exemplary components, the tracking system 302 may include other circuitry suitable for imaging such as one or more amplifiers and/or analog-to-digital converters. Further, in one embodiment, the tracking system 302 may be configured to share the operator interface 106 (see FIG. 1) and/or the display 150 (see FIG. 1) of the MRI system 100. However, in alternative embodiments, the tracking system 302 may include one or more independent displays and user interfaces (not shown in FIG. 3) for displaying the tracking information.

Accordingly, in one embodiment, the tracking controller 312 may be configured to receive a triggering signal, for example, a start-of-sequence interrupt (SSI) from the MRI system 100 indicating the onset of the imaging pulse sequence. The tracking controller 312 may then be configured to use the SSI to synchronize the imaging and tracking pulse sequences to allow for simultaneous imaging and tracking operations. To that end, in one embodiment, the tracking controller 312 may be configured to trigger the signal generator 310 to generate tracking pulses having desired signal characteristics such as shape, repetition frequency and/or timing. Particularly, in one embodiment, the tracking controller 312 may trigger the signal generator 310 to generate tracking pulses at the tracking resonant frequency different from the imaging resonant frequency. To that end, the tracking controller 312 may include one or more application-specific processors, GPUs, DSPs, microcomputers, microcontrollers, ASICs and/or FPGAs.

As previously noted, conventional MR tracking systems employ a specialized tracking sequence that includes a series of RF pulses, data acquisition (A/D) windows and separate tracking gradient waveforms implemented on an MRI system. Spatially localizing the interventional device 200 using such a conventional tracking sequence, however, entails interleaving the tracking and imaging pulses even if the tracking resonant frequency is different from the imaging resonant frequency. Unlike such conventional MR tracking techniques that interrupt the imaging sequence, the tracking system 302 employs a tracking sequence that circumvents use of separate tracking gradient waveforms. Particularly, in one embodiment, the tracking sequence includes RF tracking pulses and A/D windows such that one A/D window is applied after each tracking pulse.

To that end, in certain embodiments, the tracking controller 312 may be configured to trigger the transmitter 306 to transmit the tracking pulses such that the tracking pulse sequence is synchronized with a determined point in the imaging pulse sequence using the clock 314. In one embodiment, the determined point corresponds to the point in the imaging sequence at which the SSI is received by the tracking system 302. In certain embodiments, in addition to the SSI signal, the tracking system 302 may also receive one or more characteristics corresponding to the imaging gradient waveforms from the MRI system 100. The one or more characteristics, for example, may include amplitude, frequency, phase, timing and/or, shape of the imaging gradient waveforms. Particularly, the imaging gradient waveforms and/or corresponding characteristics may be received before, after or along with the SSI signal that allows initiation of the tracking pulse sequence.

In one embodiment, the tracking coil 204 of FIG. 2 may be specifically tuned to the tracking resonant frequency. Further, the tracking coil 204 may be configured to detect one or more response signals emitted by the tracking sample 206 (see FIG. 2) in response to the tracking pulses. It may be noted that each tracking coil 204 performs signal transmission and reception via separate transmission and reception channels 318 in the tracking system 302. Additionally, as previously noted, the transmission and reception channels 318 used for tracking the interventional device 200 may be different from the transmission and reception channels used by the MRI system 100 for imaging the target ROI.

In certain embodiments, the receiver 308 may be configured to receive the response signals from the tracking coil 204 and store the emitted signals in the memory circuitry 316. Alternatively, the receiver 308 may be configured to transmit the emitted signals to the tracking controller 312 for further processing. The tracking controller 312 may be configured to use the response signals and the received imaging gradient waveform characteristics to determine the location of the tracking sample, and thus, the location of the interventional device 200 within the patient's body.

Additionally, the tracking controller 312 may be configured to continually generate and display one or more tracking images representative of the movement of the interventional device 200 in relation to the target ROI in near real-time. To that end, the tracking controller 312 may be configured to use amplitudes of the imaging gradient waveforms for accurately overlaying the reconstructed images of the interventional device 200 over a reconstructed image of the target ROI. In one example, a common coordinate system may be used to overlay the reconstructed images of the interventional device 200 over the reconstructed image of the target ROI on the display 150.

The continual update of the tracking images allows the interventional practitioner 144 (see FIG. 1) to navigate the interventional device 200 accurately through the patient's body in near real-time. Alternatively, in certain embodiments, the tracking images may be used to allow accurate automated navigation of the interventional device 200 through the patient's body. The accurate navigation, in turn, allows the interventional practitioner 144 to provide therapy to the exact location of pathology without risking patient health. The present disclosure, thus, allows for an independent tracking system 302 that may be readily coupled to an MRI system to allow for simultaneous tracking and imaging without modifying the customary mode of operation of the MRI system 100. Certain exemplary methods for simultaneous tracking and imaging in an MRI system using an independent tracking system will be described in greater detail with reference to FIGS. 4-7.

Figure 4:
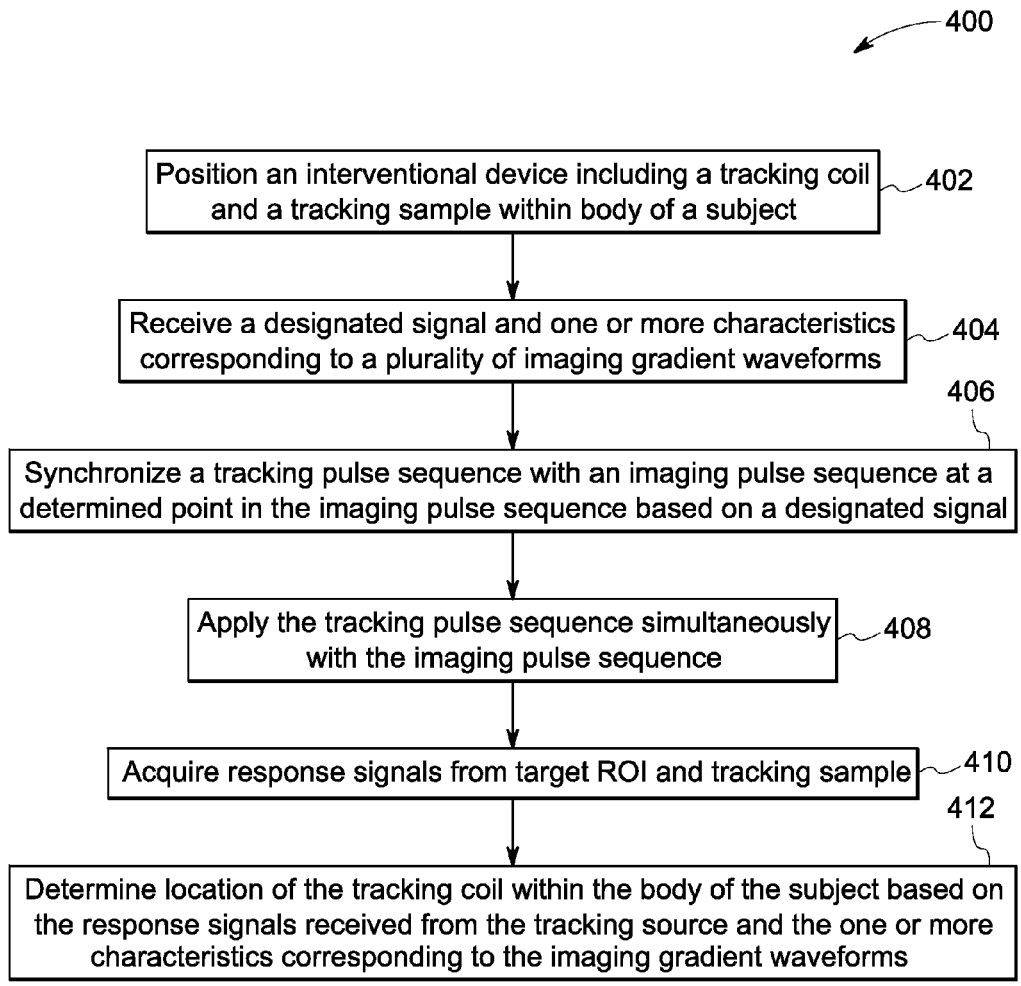
FIG. 4 is a flowchart depicting an exemplary method for tracking the interventional device, in accordance with aspects of present disclosure.

FIG. 4 illustrates a flow chart 400 depicting an exemplary method for simultaneous imaging and tracking in an MRI system, such as the MRI system 100 of FIG. 1. Embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract data types.

Embodiments of the exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 4, the exemplary method is illustrated as a collection of blocks in a logical flow chart, which represents operations that may be implemented in hardware, software, or combinations thereof. The various operations are depicted in the blocks to illustrate the functions that are performed, for example, during sequence synchronization, signal transmission and device tracking phases of the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-3.

MRI systems are widely used during interventional procedures for various diagnostic and/or therapeutic purposes. Particularly, MRI systems generate images having high spatial resolution for investigating minute features within a patient, such as, in and around a human heart. Accurate characterization of specific features, for example, corresponding to the thoracic cavity allows for a better understanding of the physiology of heart and lungs, which in turn, aids in early detection of various cardiovascular and lung diseases.

Conventionally, interventional MRI entails interleaved imaging and device tracking operations. The interleaved process prolongs scanning time, which in turn may result in patient movement including breathing and cardiac motion leading to measurement errors and scatter-related artifacts in reconstructed images. The erroneous image reconstruction, in turn, may impair determination of an appropriate diagnosis and/or treatment, thus endangering patient health.

Accordingly, embodiments of the present method describe techniques for simultaneous imaging and tracking using an independent tracking system. To that end, a patient is suitably positioned on an examination table associated with the MRI system for imaging and/or providing therapy to the target ROI, for example, the patient's spine. Particularly, the patient may be positioned such that the desired region is positioned within a FOV of the MRI system.

Further, at step 402, an interventional device, such as a needle or a catheter, is inserted into the patient's vasculature via an access site proximal or distal from the target ROI in an organ of interest of the patient. In one embodiment, for example, a catheter may be inserted into the insertion site using a guide wire and may then be advanced towards the target ROI, for example, in the cardiac, hepatic, or cranial region. Also, as previously noted, the interventional device may include a tracking coil, for example, mounted proximal to the tip of the interventional device. Additionally, the interventional device may also include a tracking sample having a resonant frequency different from an imaging resonant frequency used by the MRI system for imaging the target ROI.

In certain embodiments, the MRI system uses a plurality of gradient coils positioned about a bore of an MRI magnet to impress a polarizing magnetic field for use in imaging. Further, the MRI system may apply an imaging pulse sequence for imaging the target ROI. To that end, the imaging pulse sequence may include imaging gradient waveforms, RF pulses and A/D windows for exciting the spins capable of generating an MR signal, such as, protons found abundantly in tissues in the body. Further, the MRI system may be configured to receive response signals at the imaging resonant frequency from the target ROI emitted in response to the imaging pulses. The MRI system may also be configured to process the response signals to reconstruct an image of the target ROI.

The reconstructed MRI images may be used for providing an interventional practitioner with structural and functional information regarding the target ROI during an interventional procedure. The MR images may also allow for real-time tracking of the interventional device through the patient's body. By way of a non-limiting example, the real-time time frame for tracking corresponds to generation of a two-dimensional image approximately every 150 milliseconds, a three-dimensional image every few seconds and presentation of analysis of the acquired data every few milliseconds. To that end, the MRI system employs an independent and autonomous tracking system, such as the tracking system 302 of FIG. 3. The tracking system may be configured to generate a tracking pulse sequence at the tracking resonant frequency of the tracking sample that is coupled to the interventional device.

At step 404, a designated signal and one or more characteristics corresponding to a plurality of imaging gradient waveforms may be received by the tracking system, for example, from the MRI system or a storage repository communicatively coupled to the MRI system and/or the tracking system. The designated signal, in one embodiment, may include an SSI signal for triggering the tracking pulse sequence. Additionally, the one or more characteristics of the imaging gradient waveforms may include amplitude, frequency offset, phase, timing and/or, shape of the imaging gradient waveforms. In certain embodiments, the imaging gradient waveforms and/or corresponding characteristics may be received before, after or along with the SSI signal.

Further, at step 406, the tracking pulse sequence may be synchronized with the imaging pulse sequence at a determined point in the imaging pulse sequence based on the SSI signal. Particularly, in one example, the tracking system may be configured to synchronize the imaging pulse sequence and the tracking pulse sequence automatically. To that end, the tracking system may be configured to determine instants of time at which the RF tracking pulses and the A/D windows in the tracking pulse sequence may be applied for acquiring MR signals from the tracking sample.

At step 408, the tracking pulse sequence may be applied simultaneously with the imaging pulse sequence. In one example, the tracking system may be configured to apply the tracking pulse sequence simultaneously with the imaging pulse sequence. Subsequent to the simultaneous application of the tracking pulse sequence with the imaging pulse sequence, response signals may be acquired from the target ROI and/or the tracking sample coupled to the interventional device, as indicated by step 410. In one embodiment, the tracking system may be configured to apply a tracking A/D window after applying every RF tracking pulse to detect MR signals indicative of the movement of the interventional device.

Further, at step 412, a location of the tracking coil within or outside the patient's body may be determined based on the response signals received from the tracking sample acquired during the tracking A/D windows and one or more characteristics of the applied imaging gradient waveforms. In one example, the tracking system may be configured to determine the location of the tracking coil within the patient's body using an interventional device, such as the interventional device 200 of FIG. 2. In another example, the tracking system may be configured to determine the location of the tracking coil outside the patient's body using the interventional device positioned outside the body of the subject and configured to be combined with a suitable minimally-invasive tool such as catheter and/or a needle. Particularly, in certain embodiments, the tracking system may be configured to determine a position of the interventional device along a direction of an applied imaging gradient waveform using corresponding frequency offset and/or amplitude values.

To that end, in one embodiment, the tracking system may be configured to process the response signals received from the tracking sample to generate corresponding free induction decay (FID) signals. By way of example, the FID signals may be generated by applying an imaging gradient waveform of known direction and amplitude. The imaging gradient waveform may induce a non-equilibrium nuclear spin magnetization processing about a magnetic field, for example along a z direction to generate the FID signal. Further, in certain embodiments, the tracking system may be configured to apply a Fourier transform to the FID signals acquired in each tracking A/D window. The signal peak of a Fourier-transformed FID signal has a frequency dependence on a positional offset from the iso-center of the MRI system along the direction of the applied imaging gradient waveform. This frequency dependence, for example, may be shown using equation (1), $$\Delta f = \gamma \vec{G} \cdot \Delta \vec{r} \qquad (1)$$

where $\gamma$ is the gyromagnetic ratio of the tracking sample, $\vec{G}$ describes direction and amplitude of the applied imaging gradient waveform, $\Delta \vec{r}$ is the positional offset of the tracking sample and $\Delta f$ is a measured frequency offset from the FID signal. Specifically, equation (1) represents an example of a direct measurement of catheter position using the MR signal detected from the tracking sample under an applied gradient waveform, $\vec{G}$.

Figure 5:
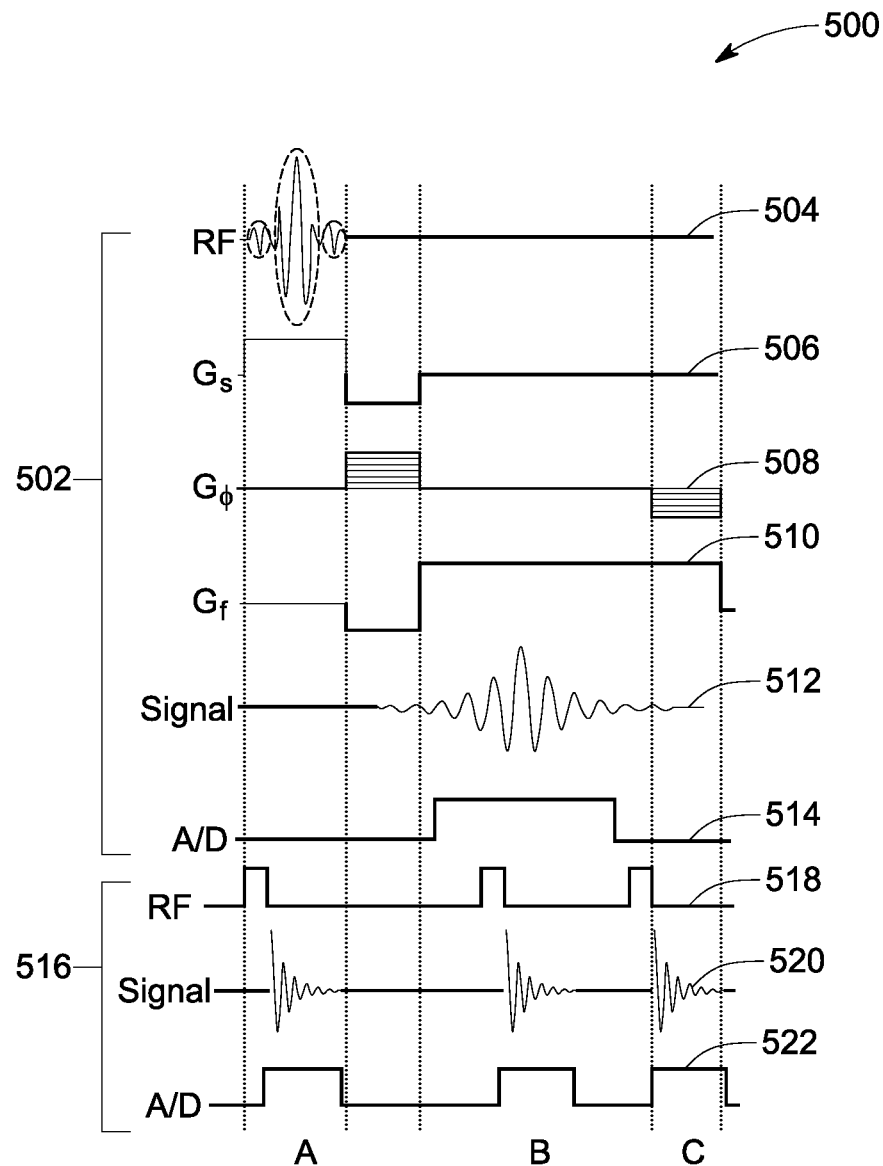
FIG. 5 is a graphical representation of exemplary pulse sequences for simultaneous MR imaging and interventional device tracking, in accordance with aspects of the present disclosure.

Further, FIG. 5 is an illustration 500 of exemplary pulse sequences for simultaneously imaging the target ROI and localizing the tracking coil position using the imaging gradient waveforms. Particularly, in accordance with certain aspects of the present disclosure, the MRI system may use an imaging pulse sequence 502 for acquiring MR response signals from the target ROI for facilitating corresponding image reconstruction. To that end, in accordance with certain aspects of the present disclosure, the imaging pulse sequence 502 may include an imaging RF excitation pulse 504, imaging gradient pulses 506, 508 and 510 applied along a plurality of directions, an MR response signal 512 and an imaging A/D window 514.

In the embodiment illustrated in FIG. 5, the imaging pulse sequence 502 corresponds to a two-dimensional fast gradient recalled echo pulse sequence. However, alternative embodiments may employ any other imaging pulse sequences, such as a fast spin echo sequence or an echo planar imaging sequence. In one embodiment, the MRI system may initiate imaging by applying the imaging RF excitation pulse 504 to an MR coil for exciting patient nuclei by producing transverse magnetization in spins located in the imaging ROI or the imaging FOV. Further, the MRI system may modulate the polarity of the gradient pulses 506-510 for modulating phase of the transverse magnetization created by the RF excitation pulse 504. In certain embodiments, the MRI system may be configured to repeat the imaging pulse sequence 502 multiple times with gradient pulses 506-510 having different polarities for each corresponding RF excitation pulse 504. Additionally, in the embodiment illustrated in FIG. 5, the gradient pulses 506-510 may be applied along logical slice, readout and a combination of readout and phase-encoding directions for each RF excitation pulse 504 for use in generating one or more images of the target ROI.

The MRI system may then acquire the response signal 512 emitted by the target ROI in response to the RF excitation pulse 504 during the imaging A/D window 514. To that end, in one embodiment, a receiving coil, such as the RF coil 124 of FIG. 1, may be tuned to receive MR signals processing at the imaging resonant frequency of the spins capable of generating an MR signal, such as human tissue, in the target ROI. The MRI system may then digitize and/or store the response signal 512 for reconstructing one or more images of the target ROI during an interventional procedure. Generally, the time needed for reconstructing the image may correspond to the number of the imaging pulse sequence 502 applications that allow acquisition of sufficient data for use in reconstructing an MR image of a desired quality. Specifically, in one embodiment, the time needed to reconstruct an image, $T_{scan}$, may be defined as a product of a repetition period, $T_R$, and a particular number of phase encoding steps, $n_y$, for a two-dimensional image.

Conventionally, after an image is acquired, a separate tracking sequence is applied. Use of the separate tracking sequence in conventional systems may provide a temporal resolution, which at best, may allow the position of the interventional device to be updated only every $T_{scan}$. In order to achieve higher temporal resolution and to avoid interleaving of imaging and tracking pulse sequences, in accordance with certain aspects of the present disclosure, a separate tracking pulse sequence 516 that is synchronized with the same repetition period, $T_R$, of the imaging sequence 502 may be employed.

Particularly, the tracking system may be configured to employ the tracking pulse sequence 516 for acquiring MR response signals from the tracking sample that is operationally coupled to the tracking coil. As previously noted, unlike conventional tracking pulses that include specialized tracking gradient waveforms, the tracking pulse sequence 516 do not include separate tracking gradient waveforms. Instead, the tracking system may be configured to use the imaging gradient waveforms of the MR imaging pulse sequence 502 for determining the tracking coil position. Particularly, the tracking system may be configured to compute the position of the tracking coil based on amplitudes of the applied imaging gradient waveforms.

To that end, in accordance with exemplary aspects of the present disclosure, the tracking system may be configured to apply the tracking pulse sequence 516 simultaneously with the imaging pulse sequence 502. Accordingly, in one embodiment, the imaging pulse sequence 502 and the tracking pulse sequence 516 may be synchronized to start at the same control clock signal, thus allowing synchronization of the tracking and imaging sequences. Further, the tracking system may be configured to determine positional and directional information corresponding to the tracking sample using the imaging gradient pulses 506-510 that are applied in parallel with the tracking pulse sequence 516 without any modifications. The ability to track the catheter position, thus, is transparent to the imaging sequence and the temporal resolution using such as independent tracking approach allows updates to the catheter position every $T_R$ period. The $T_R$ period, in certain embodiments, may be as short as 3-10 milliseconds. Further, the temporal resolution of a segment of the ROI may be defined using equation (2), $$T_R \times n_{ave}. \qquad (2)$$

where $n_{ave}$ corresponds to the number of times the tracking signals are averaged during tracking computations.

Further, in a presently contemplated approach, the tracking system may be configured to apply the tracking pulse sequence 516 within a single repetition period of the imaging pulse sequence 502. In certain other embodiments, however, the tracking system may be configured to distribute the tracking pulse sequence 516 among a plurality of repetition periods of the imaging pulse sequence 502 for acquiring tracking data from the tracking sample.

Accordingly, the tracking pulse sequence 516 may include a tracking RF excitation pulse 518 for exciting the tracking sample. Further, in accordance with exemplary aspects of the present disclosure, the tracking system may also be configured to acquire one or more response signals 520 from the tracking sample at a tracking resonant frequency that is different from the imaging resonant frequency during corresponding tracking A/D windows 522. Particularly, in one embodiment, the acquisition during each of the periods labeled A, B, and C in the tracking A/D windows 522 may be representative of positional information along the logical slice, readout, and a combination of the readout and phase-encoding directions of the imaging pulse sequence 502, respectively.

In certain embodiments, even if the applied imaging gradient waveforms for the three measurements (A, B, and C) are not completely orthogonal to one another, the tracking system may be configured to determine the positional information of the tracking coil if there are substantial components along three orthogonal directions during periods corresponding to the tracking A/D windows 522. In the embodiment illustrated in FIG. 5, the acquisition periods A and B may be employed to determine position of the tracking coil along the logical slice and readout directions, respectively. Additionally, the tracking system may be configured to apply imaging gradient waveforms along both the logical phase-encoding and the readout directions simultaneously during the tracking A/D window period C. Subsequently, the tracking system may be configured to determine a positional offset along the combined phase-encoding/readout direction (oblique direction). Specifically, a vector corresponding to the positional information may be determined using the amplitudes of the imaging gradient waveforms along two logical axes. Subsequently, the physical x, y, and z coordinates of the tracking coil may be determined based on an intersection of the positional information measured during the acquisition periods A, B, and C, and knowledge of an orientation of an imaging scan plane. Knowledge of the imaging scan plane, in turn, allows translation of the logical axis directions to physical axis directions for accurately localizing the interventional device.

Although a presently contemplated embodiment allows for simultaneous imaging and tracking, in certain embodiments, the tracking system may be configured to allow tracking of the interventional device even in absence of active imaging. To that end, the tracking system may be configured to operate in a real-time tracking-only mode with the imaging RF excitation pulse 504 and the imaging A/D window 514 turned-off, while continuing to receive characteristics of the imaging gradient pulses 506, 508 and 510. In an alternative embodiment, the tracking system 200 may be configured to dynamically swap the imaging pulse sequence 502 with the tracking pulse sequence 516, while retaining the imaging gradient pulses 506, 508 and 510 for determining the tracking coil position.

Figure 6:
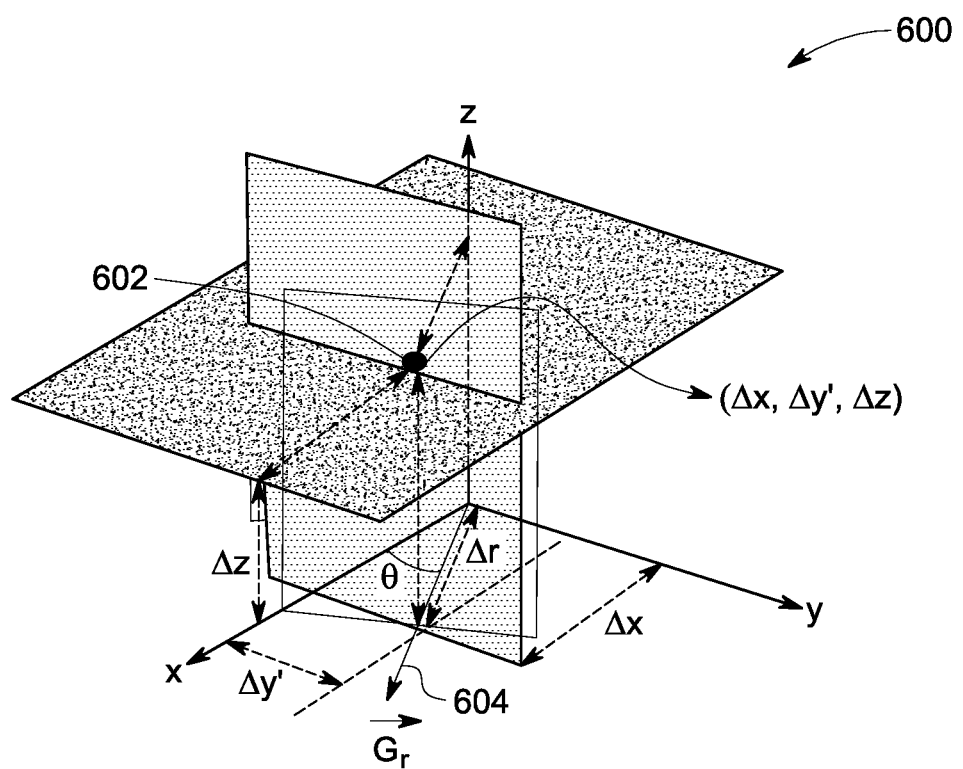
FIG. 6 is a graphical representation depicting an exemplary position of the interventional device determined using applied imaging gradient waveforms, in accordance with aspects of the present disclosure.

FIG. 6, for example, illustrates a graphical representation 600 depicting an exemplary position 602 of the tracking coil, and thereby that of the interventional device 200 (see FIG. 2), determined using the applied imaging gradient waveforms. In certain embodiments, one of the imaging gradient waveforms may be applied along an oblique direction 604, where the oblique direction 604 may be a combination of the imaging gradient waveforms applied along x and y directions. Accordingly, in the embodiment illustrated in FIG. 6, the tracking coil position 602 may be represented by an intersection of the positional offsets along the x ($\Delta x$), z ($\Delta z$), and the oblique $\vec{r}$ ($\Delta r$) directions. If the oblique direction 604 is at an angle $\theta$ to the x-axis, then the y-coordinate of the tracking coil position may be determined by equation (3):

$$\Delta y' = \Delta r \sin \theta \tag{3}$$

With returning reference to FIG. 5, in an embodiment where the tracking occurs simultaneously with imaging pulse sequence 502, only the logical slice (z), and readout (x) directions may be orthogonal. However, during acquisition period C, the resultant oblique direction may vary as the amplitude of a phase-encoding rewinder gradient. The phase-encoding rewinder gradient, for example, may be described as an imaging gradient waveform applied in the phase-encoding direction at the end of an imaging cycle to rephase the spins such that the accumulated phase (dephasing) from the (spatial) phase encoding gradient is eliminated. In the embodiment illustrated in FIG. 5, only phase accumulation from the (spatial) phase encoding gradients is eliminated (rephased) for a corresponding gradient echo pulse sequence. However, in certain other types of imaging pulse sequences, such as fast steady-state free-precession, the phase accumulation from all applied gradients during a repetition period may be rephased or reset to zero by application of rewinders or rephasing gradients.

Further, in one embodiment, variation in the resultant oblique direction with the amplitude of the phase-encoding rewinder gradient may be defined using equation (4):

$$\theta = \tan^{-1} \frac{G_x}{G'_y} \tag{4}$$

where $\theta$ is a variable angle between the oblique direction and the x-axis, $G_x$ is the imaging gradient waveform applied along the x-axis and $G'_y$ is the amplitude of the varying phase-encoding rewinder gradient at the time of measurement.

As previously noted, the imaging gradient waveform may be used to generate the FID signal. The FID signal, in turn, may be Fourier transformed to determine positional information corresponding to the tracking sample.

In certain other embodiments, however, instead of using the FID of the response signal received from the tracking sample, the tracking system may be configured to fit the phase of the response signals obtained from a plurality of measurements rather than restricting determination of the positional information to only three measurements, as shown in FIG. 5. Accordingly, the tracking system may be configured to measure signals at any time during the tracking pulse sequence 516, such as during gradient flat tops and ramps. An exemplary calculation of the position of the tracking coil by the tracking system by appropriately fitting a phase of the response signals corresponding to a plurality of measurements will be described in greater detail in the following sections.

Generally, a signal equation for a single active tracking sample may be represented as shown in equation (5):

$$\int f(\vec{r} - \vec{r}_0) \exp(i\vec{k} \cdot \vec{r}) d^3r = F(\vec{k}) \exp(i\vec{k} \cdot \vec{r}_0) \tag{5}$$

where $\vec{r}_0$ denotes a position of the tracking sample, $\vec{k}$ corresponds to a spatial frequency variable, $f(\vec{r})$ is a disposition/distribution of the tracking sample and $F(\vec{k})$ is a corresponding Fourier transform conjugate.

The spatial frequency variable $\vec{k}$ corresponding to an imaging k-space may be further defined using equation (6):

$$\vec{k} = \int \gamma G(t) dt \tag{6}$$

where $G(t)$ corresponds to the applied gradient field and $\gamma$ is the gyromagnetic ratio of the tracking sample.

In one embodiment, the applied imaging gradient field $G(t)$ may be a constant imaging gradient waveform. In an alternative embodiment, however, the applied gradient field $G(t)$ may be of an arbitrary shape and may vary in time.

Further, the relevant positional information from equation (5) may be captured in the phase term, $\exp(i\vec{k} \cdot \vec{r}_0)$, while the size and distribution of the tracking sample may modulate the signal amplitude ($R(\vec{k})$). Particularly, as previously noted, the location of the active tracking sample may be accurately determined using a simple linear least-squares fitting of the signal phase term $\exp(i\vec{k} \cdot \vec{r}_0)$. In the most general case, the signal phase may be represented, for example, as shown in equation (7).

$$\phi(t) = k(t) \cdot \vec{r} + f_{off}(\vec{r}) \cdot t \tag{7}$$

where $k(t)$ corresponds to the imaging k-space at time, t, $f_{off}(\vec{r})$ corresponds to the spatially dependent off-resonant frequency of the tracking sample and $\vec{r}$ corresponds to the position of the tracking sample.

It may be noted that $f_{off}(\vec{r})$ may account for the particular position, $\vec{r}$, of the tracking sample, where the imaging resonant frequency may be different from the tracking resonant frequency. This off-resonant frequency may be caused due to a variety of reasons, such as magnetic field inhomogeneity, and may constitute an error in the positional determination as estimated using equation (6). As such, this off-resonant frequency may contribute to an additional phase term to equation (7) that will not be dependent on the term $\exp(i\vec{k} \cdot \vec{r}_0)$.

It may be also noted that equation (7) presents an over-determined system, which may be solved for four unknowns including three terms corresponding to position coordinates $\vec{r}$ and one term corresponding to off-resonant phase accumulation ($f_{off}(\vec{r}) \cdot t$). For determining a position of the tracking sample, however, only the positional coordinate term, $\vec{r}$, may be of interest.

To that end, in one embodiment, the tracking system may be configured to consider only A/D windows with constant gradient amplitudes for determining the positional information. Additionally, the tracking system may use one or more slice-rewinding and phase encoding sections between A/D windows A and B in the tracking pulse sequence 516 for determining the positional information corresponding to the interventional device. Moreover, in certain embodiments, the tracking system may employ multiple measurements for each value of a phase-encoding gradient over a determined period of time to improve fitting statistics for equation (7). In one embodiment, the fitting statistics correspond to a least-squares error minimization approach for an over-determined system.

Figure 7:
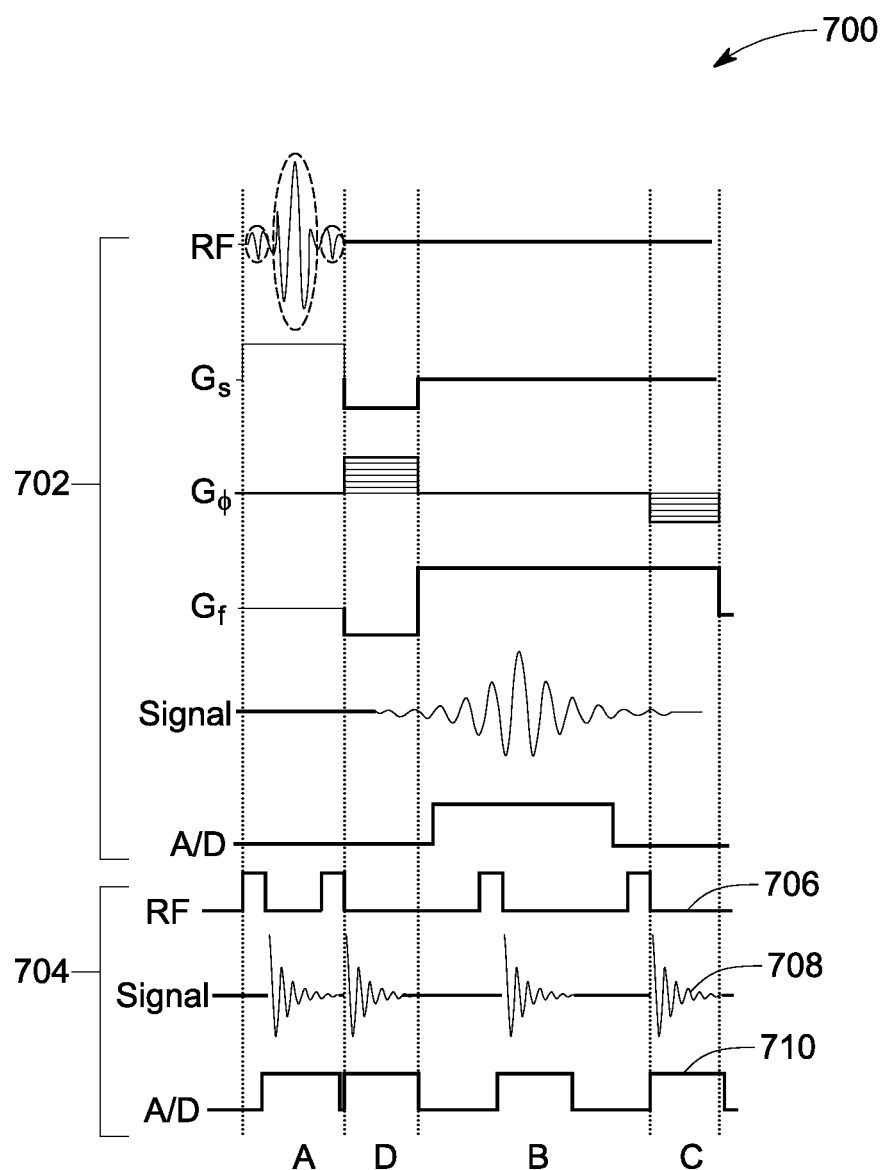
FIG. 7 is a graphical representation of another exemplary pulse sequence for simultaneous MR imaging and interventional device tracking, in accordance with aspects of the present disclosure.

Turning now to FIG. 7, an exemplary pulse sequence 700 for use in improving the fitting statistics for equation (7) is presented. The pulse sequence 700 includes an imaging pulse sequence 702 that is substantially similar to the imaging pulse sequence 502 of FIG. 5. Additionally, the pulse sequence 700 also includes a tracking pulse sequence 704 that may include a tracking RF excitation pulse 706 for exciting the tracking sample. the tracking pulse sequence 704 may also include one or more response signals 708 acquired from the tracking sample at a tracking resonant frequency that is different from the imaging resonant frequency during corresponding tracking A/D windows 710. Particularly, in one embodiment, the tracking A/D windows 710 include data acquisition periods A, B, and C, such that measurements during each of the periods A, B and C are representative of positional information along the slice, readout, and a combination of the readout and phase-encoding directions, respectively. In certain embodiments, the tracking A/D windows 710 may also include data acquisition period D during which positional information from the phase-encoding direction may also be measured.

In the embodiment illustrated in FIG. 7, the tracking system may be configured to continually use measurements corresponding to each value of the phase-encoding gradient $G\phi$, shown as the data acquisition period D, along with the acquisition periods A, B, and C for determining the changing position of the tracking sample. Further, the tracking system may use the phase of the tracking sample for providing the over-determined system from which the position $\vec{r}$ may be accurately determined using simple least-squares fitting.

Accordingly, in one example, the tracking system may be configured to measure signals indicative of positional information, $\vec{r}_0$, corresponding to the tracking coil during four tracking acquisition periods (A, B, C, D) in a single repetition period. The phase of the measured signals during each of the tracking acquisition periods (A, B, C, D) may be defined using equation (7), and may be generally represented using equations (8), (9), (10) and (11).

$$\phi_A(t) = k_A(t) \cdot \vec{r}_0 + f_{\mathit{eff}}(\vec{r}_0) \cdot t \quad (8)$$

$$\phi_B(t) = k_B(t) \cdot \vec{r}_0 + f_{\mathit{eff}}(\vec{r}_0) \cdot t \quad (9)$$

$$\phi_C(t) = k_C(t) \cdot \vec{r}_0 + f_{\mathit{eff}}(\vec{r}_0) \cdot t \quad (10)$$

$$\phi_D(t) = k_D(t) \cdot \vec{r}_0 + f_{\mathit{eff}}(\vec{r}_0) \cdot t \quad (11)$$

where $\phi_A(t)$, $\phi_B(t)$, $\phi_C(t)$ and $\phi_D(t)$ correspond to phase of the signals measured during the A, B, C and D tracking acquisition periods, respectively.

If further measurements are made during a subsequent repetition period, an additional set of measurements defined using equations (8)-(11) for the subsequent repetition period will be generated. The additional set of measurements may then result in an over-determined system having eight equations and four unknowns ($\vec{r}_0 = (x_0, y_0, z_0)$ and ($f_{\mathit{eff}}(\vec{r}) \cdot t$)).

Such an over-determined system may be defined, for example, using matrix equation (12).

$$\Phi(t) = K \cdot R_0 + \phi_{OFF} \quad (12)$$

where, $\Phi(t)$ corresponds to a matrix of signal phase measurements, K corresponds to a matrix of gradient amplitude values (from equation (6)), $R_0 = (x_0, y_0, z_0)$ corresponds to a matrix of position coordinates corresponding to the tracking coil and $\phi_{OFF} = f_{\mathit{eff}}(\vec{r}_0) \cdot t$ corresponds to an off-resonance value at the position $\vec{r}_0$.

In one embodiment, equation (12) may be solved using known techniques such as least-squares error minimization and/or matrix inversion for determining the tracking coil position.

The embodiments of FIG. 5 and FIG. 7, thus, are indicative of the flexibility provided by the present methods and systems to allow simultaneous tracking and imaging by synchronizing several tracking RF excitation and data acquisition segments with the imaging pulse sequence. As illustrated in FIG. 5 and FIG. 7, flexibility of positioning the tracking data acquisition segments at different points in the imaging pulse sequence may be provided. Furthermore, as shown in FIG. 7, an additional fourth tracking data acquisition segment D may be used in contrast to only three tracking acquisition segments illustrated in FIG. 5. As previously noted, positional information may be determined by solving the over-determined system of equation 7. Adding another data acquisition segment (D) in FIG. 7 serves to help improve the positional statistics by increasing the number of measurements.

It may be noted that the foregoing examples, demonstrations and process steps that may be performed by certain components of the present systems, for example, by the system controller 104, the processing subsystem 132 and the tracking controller 312 may be implemented by suitable code on a processor-based system, such as a general-purpose or a special-purpose computer. It may also be noted that different implementations of the present disclosure may perform some or all of the steps described herein in different orders or substantially concurrently, that is, in parallel.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of various embodiments of the present disclosure may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and techniques for use in tracking movement of the interventional device within the patient's body.

Embodiments of the present systems and methods, thus, determine position of the tracking sample, and in turn, that of the interventional device using a tracking resonant frequency that is different from the imaging resonant frequency. Use of a separate tracking resonant frequency allows for simultaneous MR tracking and imaging. The simultaneous tracking and imaging capability is very advantageous especially in emergencies such as acute stroke, brain ischemia, and intracranial hemorrhage requiring immediate and accurate interventions.

Particularly, use of an independent and self-contained tracking system that may be readily coupled to any MRI system alleviates complicated reconfiguration issues typically experienced during installation of conventional MR tracking systems. Further, the independent tracking system obviates tracking-related computations at the MRI system, thus allowing for faster imaging of the target region and rapid visualization of the interventional device position using the tracking system. The simultaneous imaging and tracking operations, thus, reduce the overall scanning time and enhance interventional practitioner and patient comfort.

Additionally, use of imaging gradient characteristics, such as phase and/or amplitude, for position tracking reduces processing time and complexity at the tracking system, while allowing for accurate determination of the location and orientation of the interventional device navigating through the patient's body. The imaging gradient characteristics may also allow the tracking system to generate integrated images that accurately represent the continually varying positions of the interventional device through the patient's body over a shared display. Particularly, the integrated images allow for accurate navigation of the interventional device within the patient's body to aid in real-time interventional procedures.

While only certain features of the present disclosure have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for simultaneous imaging and tracking, comprising:
    receiving a designated signal and one or more characteristics corresponding to a plurality of imaging gradient waveforms;
    synchronizing a tracking pulse sequence with an imaging pulse sequence at a determined point in the imaging pulse sequence based on the designated signal;
    applying the tracking pulse sequence simultaneously with the imaging pulse sequence for acquiring corresponding response signals from an interventional device, wherein the interventional device comprises at least one tracking coil and a tracking source configured to generate the response signals at a tracking resonant frequency different from an imaging resonant frequency;
    determining a location of the at least one tracking coil within or outside a body of a subject based on the response signals received from the tracking source and the one or more characteristics corresponding to the imaging gradient waveforms, wherein determining the location of the at least one tracking coil comprises:
        determining positional offsets of the at least one tracking coil along slice and readout directions of the plurality of imaging gradient waveforms;
        determining a positional offset of the at least one tracking coil along an oblique direction representative of a combination of readout and phase-encoding directions of the plurality imaging waveforms; and
        determining an intersection of the positional offsets along the slice, readout and oblique directions.

2. The method of claim 1, wherein the tracking pulse sequence comprises a plurality of tracking radiofrequency excitation pulses and a plurality of tracking data acquisition windows, and wherein the imaging pulse sequence comprises a plurality of imaging radiofrequency excitation pulses, a plurality of imaging data acquisition windows and the plurality of imaging gradient waveforms.

3. The method of claim 2, further comprising ceasing transmission of the plurality of imaging radiofrequency excitation pulses and the plurality of imaging data acquisition windows during application of the tracking pulse sequence for tracking-only operation.

4. The method of claim 2, further comprising:
    replacing the plurality of imaging radiofrequency excitation pulses with the plurality of tracking radiofrequency excitation pulses; and
    replacing the plurality of imaging data acquisition windows with the plurality of tracking data acquisition windows for tracking-only operation.

5. The method of claim 2, wherein applying the tracking pulse sequence comprises applying at least one of the plurality of data acquisition windows subsequent to application of one or more of the plurality of tracking radiofrequency excitation pulses.

6. The method of claim 1, wherein the designated signal comprises a start-of-sequence-interrupt signal received from an imaging system, a storage repository, or a combination thereof.

7. The method of claim 1, wherein the one or more characteristics of the imaging gradient waveforms comprise amplitude, frequency offset, phase, timing, or combinations thereof.

8. The method of claim 1, further comprising identifying the determined point in the imaging pulse sequence for synchronizing the tracking pulse sequence with the imaging pulse sequence based on a start-of-sequence interrupt signal.

9. The method of claim 1, wherein determining the location of the at least one tracking coil comprises:
    determining a free induction decay of a response signal received from the tracking source, based on an applied imaging gradient waveform of known direction and amplitude during a data acquisition period in the tracking pulse sequence, wherein the applied imaging gradient waveform is selected from the plurality of imaging gradient waveforms; and
    determining the location of the at least one tracking coil based on a direct Fourier transform of the free induction decay of the response signal, the known direction and amplitude of the applied imaging gradient waveform, or a combination thereof.

10. The method of claim 9, wherein the position of the at least one tracking coil along the direction of the applied imaging gradient waveform is determined using an expression:

$$\Delta f = \gamma \vec{G} \cdot \Delta \vec{r} \rightarrow \Delta \vec{r} = \frac{\Delta f}{\gamma \vec{G}},$$

wherein $\Delta f$ corresponds to a frequency offset of the Fourier transform of the free induction decay of the response signal, $\gamma$ corresponds to gyromagnetic ratio of the tracking source, $\vec{G}$ corresponds to the applied imaging gradient waveform, and $\Delta \vec{r}$ corresponds to the location of the tracking source.

11. The method of claim 1, wherein determining the location of the at least one tracking coil comprises:

measuring one or more response signals received from the tracking source during application of the plurality of imaging gradient waveforms; and determining the location of the at least one tracking coil by linear least-squares fitting of a phase of the one or more response signals, wherein the phase of the one or more response signals is defined as:

$$\phi(t) = k(t) \cdot \vec{r} + f_{off}(\vec{r}) \cdot t$$

wherein k(t) corresponds to a spatial frequency variable $\vec{k}$ corresponding to an imaging k-space at time, t, $f_{off}(\vec{r})$ corresponds to a spatially dependent off-resonant frequency of the tracking source, and $\vec{r}$ corresponds to a particular position of the tracking source.

12. The method of claim 1, wherein the imaging pulse sequence comprises a fast gradient recalled echo sequence, a fast spin echo sequence, an echo planar imaging sequence, or combinations thereof.

13. The method of claim 1, further comprising applying the tracking pulse sequence within a single imaging pulse sequence repetition period.

14. The method of claim 1, wherein applying the tracking pulse sequence comprises distributing application of the tracking pulse sequence among one or more imaging pulse sequence repetition periods.

15. The method of claim 1, wherein determining the location of the at least one tracking coil within the body of the subject comprises using a least-squares fitting of accumulated phase of signals measured in a plurality of data acquisition periods within at least a single tracking pulse sequence repetition period.

16. The method of claim 1, wherein determining the location of the at least one tracking coil within the body of the subject comprises using a least-squares fitting of accumulated phase of signals measured in a plurality of data acquisition periods within multiple tracking pulse sequence repetition periods.

17. The method of claim 1, further comprising generating one or more images representative of the determined location of the at least one tracking coil within the body of the subject.

18. A tracking system, comprising:
an interventional device configured to be inserted into a body of a subject;
at least one tracking coil operatively coupled to the interventional device;
a tracking source operatively coupled to one or more of the interventional device and the at least one tracking coil and configured to generate a magnetic resonance signal at a tracking resonant frequency different from an imaging resonant frequency;
at least one processing subsystem configured to:
receive a designated signal and one or more characteristics corresponding to a plurality of imaging gradient waveforms;
synchronize a tracking pulse sequence with an imaging pulse sequence at a determined point in the imaging pulse sequence based on the designated signal;
apply the tracking pulse sequence simultaneously with the imaging pulse sequence for acquiring corresponding response signals from the tracking source at the tracking resonant frequency; and
determine a location of the at least one tracking coil within or outside the body of the subject based on the response signals received from the tracking source and the one or more characteristics corresponding to the imaging gradient waveforms, wherein determining the location of the at least one tracking coil comprises determining positional offsets of the at least one tracking coil along slice and readout directions of the plurality of imaging gradient waveforms, determining a positional offset of the at least one tracking coil along an oblique direction representative of a combination of readout and phase-encoding directions of the plurality of imaging gradient waveforms, and determining an intersection of the positional offsets along the slice, the readout and the oblique directions.

19. The system of claim 18, wherein the interventional device comprises a catheter, a needle, a laparoscope, an endoscope, a stent, a shunt, a guidewire, a catheter sheath, or combinations thereof.

20. The system of claim 18, wherein the interventional device is configured to be manipulated from outside the body of the subject.

21. The system of claim 20, wherein the interventional device comprises an external interventional device positioned outside the body of the subject and configured to be combined with a catheter, a needle, a laparoscope, an endo scope, a stent, a shunt, a guidewire, a catheter sheath, a biopsy guidance device, or combinations thereof.

22. The system of claim 18, further comprising one or more transmit and receive channels configured to transmit and receive the tracking pulse sequence different from transmit and receive channels configured to transmit and receive the imaging pulse sequence.

23. The system of claim 18, further comprising a plurality of tracking coils mounted on the interventional device.

24. The system of claim 18, wherein the tracking source is positioned in an annular ring encapsulated within the at least one tracking coil.

25. The system of claim 18, wherein the tracking source is positioned in an annular ring embedded within the at least one tracking coil.

26. The system of claim 18, wherein the at least one tracking coil is wrapped around the interventional device.

27. The system of claim 18, wherein the at least one tracking coil is configured to transmit magnetic resonance signals, receive magnetic resonance signals from the tracking source, or a combination thereof.

28. The system of claim 18, wherein the tracking source comprises a material having a gyromagnetic ratio different from the gyromagnetic ratio of hydrogen.

29. The system of claim 18, wherein the tracking source comprises a material having a spin density different from the spin density of hydrogen.

30. The system of claim 18, wherein the tracking source comprises deuterium, carbon, sodium, phosphorous, oxygen, helium-3, xenon or fluorine.

31. A magnetic resonance imaging system, comprising:
a scanner comprising a plurality of coils configured to generate a magnetic field, one or more gradient fields and a plurality of radiofrequency signals within the magnetic field;
a processing subsystem configured to process magnetic resonance signals emitted from a target region of interest of a subject positioned in the magnetic field in response to the plurality of radiofrequency signals and generate one or more corresponding images of the target region of interest;
an interventional device configured to be inserted into a body of the subject;
a tracking source operatively coupled to the interventional device and configured to generate a magnetic resonance signal at a tracking resonant frequency different from an imaging resonant frequency in response to the plurality of radiofrequency signals;

at least one tracking coil operationally coupled to the interventional device and configured to receive the magnetic resonance signal from the tracking source;

a tracking subsystem comprising at least one tracking controller communicatively coupled to the processing subsystem, wherein the tracking controller is configured to:

receive a designated signal and one or more characteristics corresponding to a plurality of imaging gradient waveforms;

synchronize a tracking pulse sequence with an imaging pulse sequence at a determined point in the imaging pulse sequence based on the designated signal;

apply the tracking pulse sequence simultaneously with the imaging pulse sequence for acquiring corresponding response signals from the tracking source at the tracking resonant frequency;

determine a location of the at least one tracking coil within or outside the body of the subject based on the response signals received from the tracking source and the one or more characteristics of the imaging gradient waveforms, wherein determining the location of the at least one tracking coil comprises determining positional offsets of the at least one tracking coil along slice and readout directions of the plurality of imaging gradient waveforms, determining a positional offset of the at least one tracking coil along an oblique direction representative of a combination of readout and phase-encoding directions of the plurality of imaging gradient waveforms, and determining an intersection of the positional offsets along the slice, the readout and the oblique directions;

generate one or more images representative of the determined location of the at least one tracking coil within the body of the subject for display; and a display device configured to display the one or more images of the target region of interest, the determined location of the at least one tracking coil, or a combination thereof.

32. A non-transitory computer readable medium that stores instructions executable by one or more processors to perform a method for simultaneous imaging and tracking, comprising:

receiving a designated signal and one or more characteristics corresponding to a plurality of imaging gradient waveforms;

synchronizing a tracking pulse sequence with an imaging pulse sequence at a determined point in the imaging pulse sequence based on the designated signal;

applying the tracking pulse sequence simultaneously with the imaging pulse sequence for acquiring corresponding response signals from an interventional device, wherein the interventional device comprises at least one tracking coil and a tracking source configured to generate the response signals at a tracking resonant frequency different from an imaging resonant frequency;

determining a location of the at least one tracking coil within or outside body of a subject based on the response signals received from the tracking source and the one or more characteristics corresponding to the imaging gradient waveforms, wherein determining the location of the at least one tracking coil comprises:

determining positional offsets of the at least one tracking coil along slice and readout directions of the plurality of imaging gradient waveforms;

determining a positional offset of the at least one tracking coil along an oblique direction representative of a combination of readout and phase-encoding directions of the plurality of imaging gradient waveforms; and determining an intersection of the positional offsets along the slice, the readout and the oblique directions.

* * * * *